US012428401B2

(12) United States Patent
Oh et al.

(10) Patent No.: US 12,428,401 B2
(45) Date of Patent: Sep. 30, 2025

(54) SALT OF AN AMINOPYRIDINE DERIVATIVE COMPOUND, A CRYSTALLINE FORM THEREOF, AND A PROCESS FOR PREPARING THE SAME

(71) Applicant: Yuhan Corporation, Seoul (KR)

(72) Inventors: Sang Ho Oh, Gyeonggi-do (KR); Jong Gyun Kim, Gyeonggi-do (KR); Se-Woong Oh, Gyeonggi-do (KR); Tae Dong Han, Gyeonggi-do (KR); Soo Yong Chung, Gyeonggi-do (KR); Seong Ran Lee, Gyeonggi-do (KR); Kyeong Bae Kim, Seoul (KR); Young Sung Lee, Seoul (KR); Woo Seob Shin, Gyeonggi-do (KR); Hyun Ju, Gyeonggi-do (KR); Jeong Ki Kang, Gyeonggi-do (KR); Su Min Park, Chungcheongbuk-do (KR); Dong Kyun Kim, Gyeonggi-do (KR)

(73) Assignee: Yuhan Corporation, Seoul (KR)

( * ) Notice: Subject to any disclaimer, the term of this patent is extended or adjusted under 35 U.S.C. 154(b) by 0 days.

(21) Appl. No.: 18/618,379

(22) Filed: Mar. 27, 2024

(65) Prior Publication Data

US 2024/0279203 A1    Aug. 22, 2024

Related U.S. Application Data

(63) Continuation of application No. 17/697,655, filed on Mar. 17, 2022, now Pat. No. 11,981,659, which is a continuation of application No. 16/605,944, filed as application No. PCT/KR2018/004473 on Apr. 18, 2018, now Pat. No. 11,453,656.

(30) Foreign Application Priority Data

Apr. 21, 2017 (KR) .......................... 10-2017-0051687

(51) Int. Cl.
| | |
|---|---|
| C07D 403/04 | (2006.01) |
| A61K 31/5377 | (2006.01) |
| A61P 35/00 | (2006.01) |
| C07C 303/22 | (2006.01) |
| C07C 309/04 | (2006.01) |
| C07D 413/14 | (2006.01) |

(52) U.S. Cl.
CPC .......... *C07D 403/04* (2013.01); *C07C 303/22* (2013.01); *C07C 309/04* (2013.01); *C07B 2200/13* (2013.01)

(58) Field of Classification Search
CPC .. C07D 403/04; C07D 413/14; C07C 303/22; C07C 309/04; C07B 2200/13; A61P 35/00; A61K 31/5377
See application file for complete search history.

(56) References Cited

U.S. PATENT DOCUMENTS

| | | |
|---|---|---|
| 9,006,448 B2 | 4/2015 | Reddy et al. |
| 9,453,011 B2 | 9/2016 | Lao et al. |
| 2007/0078159 A1 | 4/2007 | Matsushima |
| 2010/0029610 A1 | 2/2010 | Singh et al. |
| 2011/0281841 A1 | 11/2011 | Lee et al. |
| 2014/0148601 A1 | 5/2014 | Reddy et al. |
| 2016/0102076 A1 | 4/2016 | Suh et al. |
| 2017/0166598 A1 | 6/2017 | Huang et al. |
| 2021/0130318 A1 | 5/2021 | Butterworth et al. |
| 2021/0139461 A1 | 5/2021 | Oh et al. |
| 2023/0021395 A1 | 1/2023 | Oh et al. |

FOREIGN PATENT DOCUMENTS

| | | |
|---|---|---|
| CN | 104788427 A | 7/2015 |
| JP | 4648835 B2 | 3/2011 |
| JP | 7126514 B2 | 8/2022 |
| KR | 10-2017-0051687 A | 5/2017 |
| WO | 2005/077933 A1 | 8/2005 |
| WO | 2011/023146 A1 | 3/2011 |
| WO | 2011/060295 A1 | 5/2011 |
| WO | 2013/014448 A1 | 1/2013 |
| WO | 2015/003571 A1 | 1/2015 |
| WO | 2015/175632 A1 | 11/2015 |
| WO | 2016/060443 A2 | 4/2016 |
| WO | 2018/194356 A1 | 10/2018 |
| WO | 2020/079637 A1 | 4/2020 |

OTHER PUBLICATIONS

Balbach et al., Pharmaceutical evaluation of early development candidates "The 100 mg approach", International Journal of Pharmaceutics, 2004, vol. 275, pp. 1-12.
Bastin et al: "Salt Selection and Optimisation Procedures for Pharmaceutical New Chemical Entities", Organic Process Research & Development, vol. 4, No. 5, Jul. 19, 2000, pp. 427-435.
Berg, S. et al., "Pharmaceutical Salts" Journ. of Pharm. Sciences, 1977, 66:1-19, & Handbook of Pharmaceutical Salts, Properties, Selection & Use, Stahl and Wermuth, Eds., Wiley-VCH and VHCA, Zurich.
Berge, et al., "Pharmaceutical Salts," Journal of Pharmaceutical Sciences, 66(1): 1-19 (1977).

(Continued)

*Primary Examiner* — Sun Jae Yoo
(74) *Attorney, Agent, or Firm* — BakerHostetler (57) ABSTRACT

The present invention relates to novel mesylate salt of N-(5-(4-(4-((dimethylamino)methyl)-3-phenyl-1H-pyrazol-1-yl)pyrimidine-2-ylamino)-4-methoxy-2-morpholinophenyl)acrylamide, a novel crystalline form thereof, and a process for preparing the same. More specifically, the present invention relates to mesylate salt of N-(5-(4-(4-((dimethylamino)methyl)-3-phenyl-1H-pyrazol-1-yl)pyrimidine-2-ylamino)-4-methoxy-2-morpholinophenyl)acrylamide, which is excellent in stability, solubility, and bioavailability when it is administered not only alone but also in combination with other drugs and which has a high purity, a crystalline form thereof, and a process for preparing the same.

8 Claims, 7 Drawing Sheets

(56) References Cited

OTHER PUBLICATIONS

Brittain, "Polymorphism in Pharmaceutical Solids", Preface, Second Edition, Drug and the Pharmaceutical Sciences, vol. 192, 2009.
Caira M R, "Crystalline Polymorphism of Organic Compounds", Topics in Current Chemistry, Springer, Berlin, DE, (Jan. 1, 1998), vol. 198, ISSN 0340-1022, pp. 163-208.
Elder et al., "Use of pharmaceutical salts and cocrystals to address the issue of poor solubility", International Journal of Pharmaceutics. vol. 453, Is. 1., 2012, pp. 88-100.
Gould et al: "Salt selection for basic drugs", International Journal of Pharmaceutics, vol. 33, No. 1-3, Nov. 1, 1986, pp. 201-217.
Serajuddin et al: "Salt formation to improve drug solubility", Advanced Drug Delivery Reviews, 59 (7), 2007, pp. 603-616,, Nov. 10, 2020, Science Direct, 603-616, 59.
Serajuddin, "Salt formation to improve drug solubility", Advanced Drug Delivery Reviews 59, 2007, pp. 603-616.
Singhal et al., "Drug polymorphism and dosage form design: a practical perspective", Advanced Drug Delivery Reviews, 2004, 56, 335-347.
Stahl P H et al: "chapter 12: Monographs on acids and bases", Jan. 1, 2002, Handbook of Pharmaceutical Salts : Properties, Selection, and Use, Helvetica Chimica Acta ; pp. 265-327.
Yu et al: "Physical characterization of polymorphic drugs: an integrated characterization strategy", Pharmaceutical Science & Technology Today, Jun. 1998, vol. 1, Issue 3, pp. 118-127.

SALT OF AN AMINOPYRIDINE DERIVATIVE COMPOUND, A CRYSTALLINE FORM THEREOF, AND A PROCESS FOR PREPARING THE SAME

CROSS-REFERENCE TO RELATED APPLICATIONS

The present application is a continuation U.S. Ser. No. 17/697,655, filed on Mar. 17, 2022, which is a divisional of U.S. Ser. No. 16/605,944, filed Oct. 17, 2019, which is the National Stage of International Patent Application No. PCT/KR2018/004473, filed Apr. 18, 2018, which claims the benefit of Korean application number 10-2017-0051687, filed Apr. 21, 2017, the entire contents of each of which are incorporated herein by reference.

TECHNICAL FIELD

The present invention relates to mesylate(methanesulfonate) salt of the compound of N-(5-(4-(4-((dimethylamino)methyl)-3-phenyl-1H-pyrazol-1-yl)pyrimidine-2-ylamino)-4-methoxy-2-morpholinophenyl)acrylamide in the form of a free base represented by the following Formula 2, a crystalline form thereof, and a process for preparing the same. More specifically, the present invention relates to the mesylate salt of the compound represented by the following Formula 2, which is excellent in stability, solubility, and bioavailability and has a high purity, a crystalline form thereof, and a process for preparing the same.

[Formula 2]

BACKGROUND ART

Globally, lung cancer accounts for about one-third of the causes of cancer death, and non-small cell lung cancer accounts for about 80% of the entire lung cancer. Only some of the patients suffering from non-small cell lung cancer are expected to be cured by surgery, and most patients are diagnosed to have locally advanced cancer or metastatic cancer. Treatment of advanced non-small cell lung cancer hinges on the presence or absence of molecular markers of specific mutations. If an epidermal growth factor receptor (EGFR) mutation is positive, the first-line treatment is an EGFR tyrosine kinase inhibitor (TKI). Patients with these mutations are susceptible to EGFR TKIs. However, most patients responding to EGFR TKIs (e.g., erlotinib and gefitinib) eventually become resistant thereto and are exacerbated to advanced lung cancer. Among these causes, T790M, which is a point mutation in the gatekeeper residue of the tyrosine kinase (TK) domain, accounts for about 50 to 60% of the acquired resistance. Thus, a molecular targeted therapeutic agent for this mutation is under development. In addition, although about 50% of the patients suffering from non-small cell lung cancer with an EGFR mutation develop brain metastasis within 3 years from the diagnosis, the EGFR TKIs developed up to the present have a low permeability in the brain, so that the treatment for brain metastasis lesions is limited.

The compound of N-(5-(4-(4-((dimethylamino)methyl)-3-phenyl-1H-pyrazol-1-yl)pyrimidine-2-ylamino)-4-methoxy-2-morpholinophenyl)acrylamide in the form of a free base as mentioned above is known to have few impacts on wild-type EGFR and to be a highly selective and irreversible EGFR TKI with a strong inhibitory activity against single mutation of T790M and dual mutations (EGFRm). The compound is expected to have a therapeutically effective efficacy in the treatment of patients with advanced non-small cell lung cancer as primary cancer and advanced non-small cell lung cancer with brain metastasis.

In this regard, International Patent Publication WO 2016-060443 discloses the compound represented by the above Formula 2 and a process for preparing it, wherein the compound can be used as a drug to inhibit the activity of protein kinase-mediated disorders, especially EGFR having one or more mutations, as compared with the wild-type EGFR. Thus, this compound has a potential as a candidate for the development of drugs for the treatment of protein kinase-mediated disorders.

DISCLOSURE OF INVENTION

Technical Problem

When the potential for a compound to be developed as a drug is determined, a high pharmacological activity and a good pharmacological profile are not the sole factors to be taken into account. A good drug candidate must have few amounts of impurities, be physically and chemically stable, and show an allowable level of bioavailability. Since the compound of N-(5-(4-(4-((dimethylamino)methyl)-3-phenyl-1H-pyrazol-1-yl)pyrimidine-2-ylamino)-4-methoxy-2-morpholinophenyl)acrylamide in the form of a free base has not only a low solubility in water but also a low solubility in an acidic environment, this compound has a disadvantage in that the solubility and the bioavailability thereof is not excellent when it is used as a drug. Thus, there has been a challenge to prepare a formulation of this compound, which is excellent in solubility and bioavailability as compared with the free base form.

Accordingly, it is an object of the present invention to provide a pharmaceutically acceptable salt of the compound of N-(5-(4-(4-((dimethylamino)methyl)-3-phenyl-1H-pyrazol-1-yl)pyrimidine-2-ylamino)-4-methoxy-2-morpholinophenyl)acrylamide, in which various physicochemical problems such as solubility and hygroscopicity are improved, in order to increase the solubility and the bioavailability of the compound in the form of a free base. That is, as a result of animal testing of the compound in the form of a free base having a low solubility, there has been a problem that a low absorption rate of the drug and variations in the absorption rate between individuals were observed. Accordingly, in order to solve this problem, it is an object of the present invention to provide a pharmaceutically acceptable salt of the compound in the form of a free base and a crystalline form thereof, whose solubility and bioavailability are improved.

Meanwhile, the majority of patients suffering from protein kinase-mediated disorders are accompanied by such gastrointestinal diseases as reflux esophagitis, dyspepsia, and gastritis. In such event, in order to prevent gastric acid stimulation, a drug, for example, a proton pump inhibitor such as esomeprazole or an H2-receptor antagonist such as cimetidine, is frequently prescribed in combination with a drug for the treatment of protein kinase-mediated disorders.

However, in the case where a drug for treating protein kinase-mediated disorders is administered in combination with the drug for preventing gastric acid stimulation, there is a problem that the absorption rate of the drug for treating protein kinase-mediated disorders may be changed by the interaction between the drugs.

Specifically, in the case where a drug for treating protein kinase-mediated disorders is administered in combination with the drug for preventing gastric acid stimulation, there has been a problem that the plasma concentration of the drug for treating protein kinase-mediated disorders is decreased, so that its plasma concentration is lower than the effective therapeutic range thereof.

Accordingly, it is another object of the present invention to provide a pharmaceutically acceptable salt of the compound in the form of a free base and a crystalline form thereof, which are excellent in bioavailability, even when they are administered together with a drug that is likely to be administered in combination with the drug for treating protein kinase-mediated disorders in clinical practice and prevents gastric acid stimulation (for example, a proton pump inhibitor or an H2 receptor antagonist).

As a result of achieving the above object, it is possible to reduce the impacts of food or an antacid to be taken by a patient on the drug absorption, which otherwise may be a problem in clinical practice.

Solution to Problem

According to one aspect of the present invention, there is provided mesylate salt of N-(5-(4-(4-((dimethylamino)methyl)-3-phenyl-1H-pyrazol-1-yl)pyrimidine-2-ylamino)-4-methoxy-2-morpholinophenyl)acrylamide, as represented by the following Formula 1:

[Formula 1]

In addition, according to another aspect of the present invention, there is provided a process for preparing the mesylate salt represented by the following Formula 1, which comprises: (1) mixing the compound represented by the following Formula 2 and a single organic solvent or a mixed solvent, followed by adding methanesulfonic acid thereto, to prepare a mixture of the mesylate salt represented by the Formula 1; and (2) adding an organic solvent to the mixture to crystallize the mesylate salt represented by the Formula 1:

[Formula 1]

[Formula 2]

According to another aspect of the present invention, there is provided a pharmaceutical composition for treating a protein kinase-mediated disorder, which comprises the mesylate salt and a pharmaceutically acceptable additive.

In addition, according to another aspect of the present invention, there is provided a pharmaceutical composition for inhibiting the activity of epidermal growth factor receptor (EGFR) having one or more mutations as compared with wild-type EGFR, which comprises the mesylate salt and a pharmaceutically acceptable additive.

Advantageous Effects of Invention

The mesylate salt compound and a crystalline form thereof provided by the present invention have advantages in that they are excellent in stability, solubility, and bioavailability as compared with other pharmaceutically acceptable salts, have a high purity, and produce the excellent bioavailability as mentioned above when they are administered not only alone but also in combination with an antacid. In addition, the preparation process provided by the present invention has an advantage in that it is possible to produce the mesylate salt compound having the above advantages on a large scale.

BEST MODE FOR CARRYING OUT THE INVENTION

Term Description

Unless otherwise stated or defined, all technical and scientific terms used herein have the meaning commonly understood by one of ordinary skill in the art to which this invention pertains.

Unless otherwise stated, all percentages, parts, and ratios are by weight.

In this specification, when a part is referred to as "comprising" an element, it is to be understood that the part may comprise other elements as well, rather than exclude the other elements, unless specifically stated otherwise.

All numbers expressing quantities in connection with components, properties such as molecular weights, reaction conditions, and the like used herein are to be understood as being modified in all instances by the term "about."

Hereinafter, the present invention will be described in detail.

The present invention relates to mesylate salt of N-(5-(4-(4-((dimethylamino)methyl)-3-phenyl-1H-pyrazol-1-yl)pyrimidine-2-ylamino)-4-methoxy-2-morpholinophenyl)acrylamide, as represented by the following Formula 1.

[Formula 1]

The present inventors have newly synthesized mesylate salt of the compound of N-(5-(4-(4-((dimethylamino)methyl)-3-phenyl-1H-pyrazol-1-yl)pyrimidine-2-ylamino)-4-methoxy-2-morpholinophenyl)acrylamide, which is excellent in solubility and bioavailability as compared with the compound of N-(5-(4-(4-((dimethylamino)methyl)-3-phenyl-1H-pyrazol-1-yl)pyrimidine-2-ylamino)-4-methoxy-2-morpholinophenyl)acrylamide in the form of a free base, which is excellent in stability, solubility, and bioavailability as compared with other pharmaceutically acceptable salts of the compound, and which has a high purity, thereby completing the present invention.

In general, hydrochloride salts account for the largest proportion of the salts of commercially available compounds approved by the FDA. Then, sulfates, bromides, chlorites, tartrates, phosphates, citrates, and malates account for large proportions in their order. Mesylate salts account for only about 2%. That is, a mesylate salt of a particular compound is not generally a selectable salt. But, the present inventors have found through repeated researches that mesylate salt of N-(5-(4-(4-((dimethylamino)methyl)-3-phenyl-1H-pyrazol-1-yl)pyrimidine-2-ylamino)-4-methoxy-2-morpholinophenyl)acrylamide is excellent in stability, solubility, and bioavailability as compared with other pharmaceutically acceptable salts and has a high purity. In addition, the present inventors have carried out a lot of researches for the preparation thereof on a large scale. As a result, the present inventors have completed the present invention.

In one aspect of the present invention, the mesylate salt represented by the above Formula 1 is characterized in that it is in a crystalline form, and the crystalline form falls within the scope of the present invention. Crystalline forms of a pharmaceutical compound may be important in the development of suitable formulations. Certain crystalline forms may be improved in solubility, stability, and bioavailability, and have a high purity as compared with other crystalline forms. Thus, they can be selected as good drug candidates. Certain crystalline forms have an advantage in that it is improved in thermodynamic stability.

Figure 1:
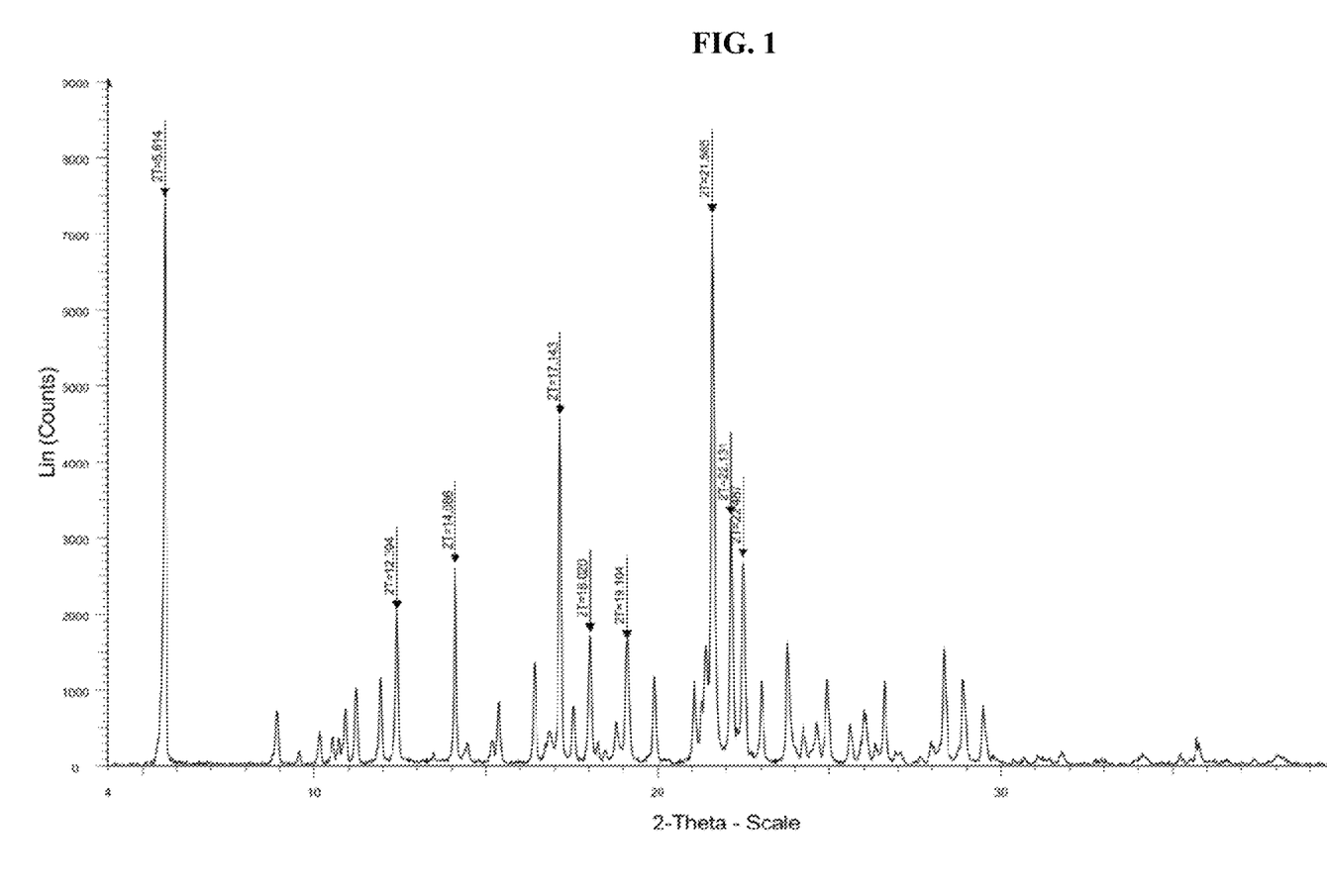
FIG. 1 is a powder X-ray diffraction (PXRD) graph of the compound prepared in Example 1 of the present invention.

In one aspect of the present invention, the crystalline form of the mesylate salt represented by the above Formula 1 may be a crystalline form (I). It is preferable that the diffraction peaks in a PXRD graph are present at 2θ (theta) angles of 5.614±0.2, 12.394±0.2, 14.086±0.2, 17.143±0.2, 18.020±0.2, 19.104±0.2, 21.585±0.2, 22.131±0.2, and 22.487±0.2 degrees; and it is more preferable that the diffraction peaks in a PXRD graph are present at 2θ angles of 5.614, 12.394, 14.086, 17.143, 18.020, 19.104, 21.585, 22.131, and 22.487 degrees. But the present invention is not limited thereto.

Figure 2:
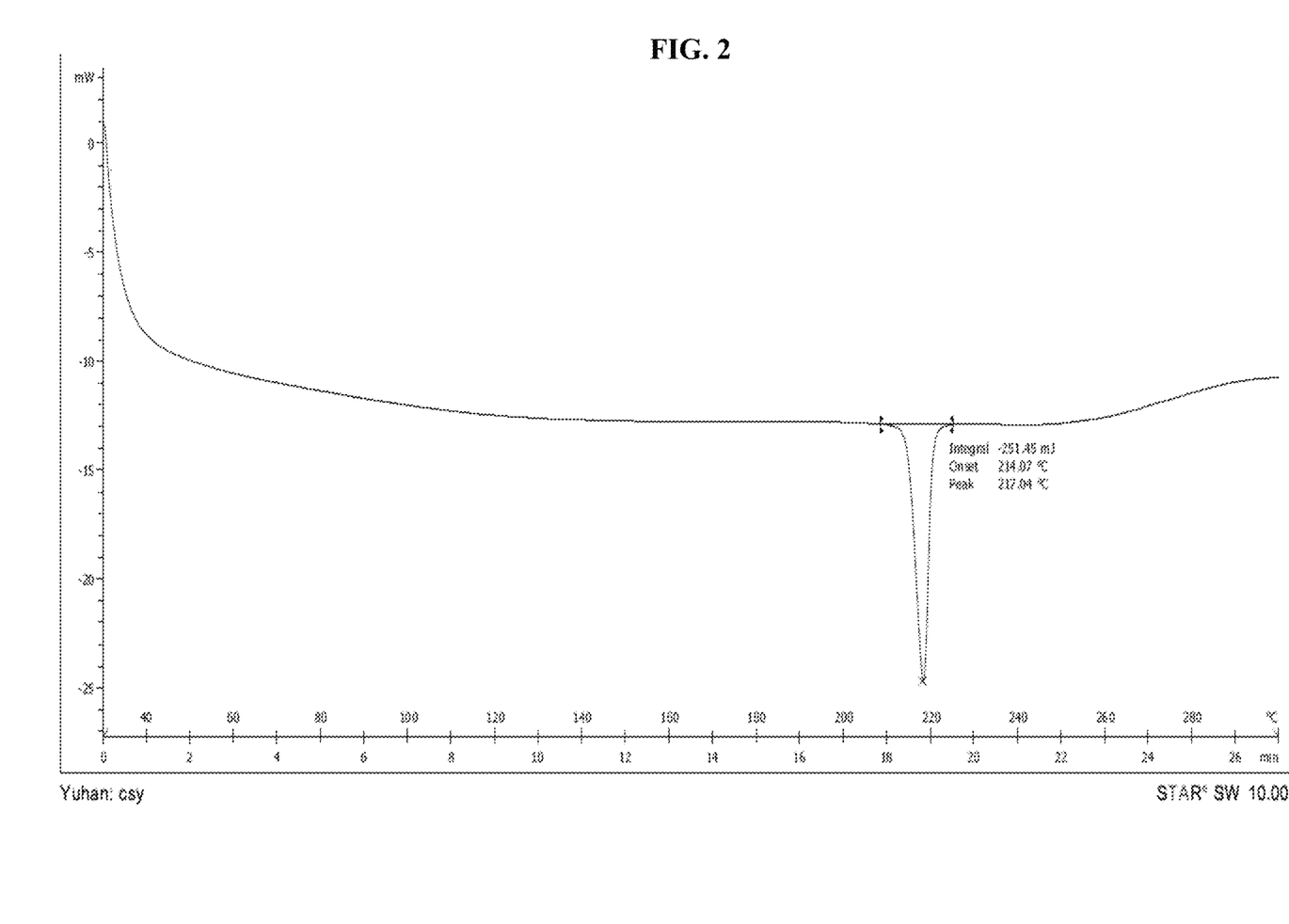
FIG. 2 is a differential scanning calorimetry (DSC) graph of the compound prepared in Example 1 of the present invention.

In another aspect of the present invention, the crystalline form (I) of the mesylate salt represented by the above Formula 1 may have an endothermic transition peak value at 210 to 230° C., preferably 217±2° C., in a DSC (differential scanning calorimetry) graph; and it is preferable that the onset is 214±2° C. But the present invention is not limited thereto.

In addition, the present invention relates to a process for preparing the mesylate salt represented by the following Formula 1, which comprises: (1) mixing the compound represented by the following Formula 2 and a single organic solvent or a mixed solvent, followed by adding methanesulfonic acid thereto, to prepare a mixture of the mesylate salt represented by the Formula 1; and (2) adding an organic solvent to the mixture to crystallize the mesylate salt represented by the Formula 1:

[Formula 1]

[Formula 2]

The crystalline form (I) of the mesylate salt represented by the above Formula 1 may be prepared by this preparation process. But the present invention is not limited thereto.

In one aspect of the present invention, the single organic solvent of the step (1) is not particularly limited as long as it is suitable for the present invention. And it is preferably one selected from the group consisting of acetone, methyl ethyl ketone, and ethyl acetate. If this single organic solvent is used, it is advantageous in that the crystalline form (I) of the mesylate salt represented by the above Formula 1 can be stably produced.

In another aspect of the present invention, the mixed solvent of the step (1) may be a mixed solvent of water and at least one suitable organic solvent. Specifically, it is preferably a mixed solvent of water and at least one organic solvent selected from acetone and methyl ethyl ketone. But the present invention is not limited thereto. If this mixed solvent is used, it is advantageous in that the crystalline form (I) of the mesylate salt represented by the above Formula 1 can be stably produced.

In another aspect of the present invention, the mixed ratio of water and the organic solvent may be 1:1 to 1:10, specifically 1:4 to 1:6, by volume. But the present invention is not limited thereto.

In one aspect of the present invention, the step (1) may be carried out at a temperature of 20 to 70° C., preferably at a temperature of 45 to 60° C. Within the above temperature range, it is advantageous in the improvement of the quality of the crystalline form (I) of the mesylate salt represented by the above Formula 1.

Meanwhile, the step (2) is a step to crystallize the mesylate salt represented by the Formula 1 by adding an organic solvent to the mixture thereof. Specifically, in the step (2), the mesylate salt represented by the Formula 1 may be crystallized by adding an organic solvent to the mixture thereof, stirring the resulting mixture, cooling and filtering the mixture, and drying the resulting solid.

In one aspect of the present invention, the organic solvent used in the step (2) may be same as and different from the single organic solvent used in the step (1). Specifically, the organic solvent used in the step (2) may be at least one selected from the group consisting of acetone, methyl ethyl ketone, and ethyl acetate. But the present invention is not limited thereto.

In addition, in the step (2), the organic solvent may be added in a volume ranging from 3 mL to 20 mL based on 1 g of the compound represented by the Formula 2. Specifically, in the step (2), the organic solvent may be added in a volume ranging from 5 mL to 20 mL, more specifically, in a volume ranging from 5 mL to 10 mL based on 1 g of the compound represented by the Formula 2. But the present invention is not limited thereto. When the organic solvent is added in the above volume, it is advantageous in that the reduction of the yield of the crystalline form (I) of the mesylate salt represented by the above Formula 1 can be minimized.

In another aspect of the present invention, the mixture may be cooled to a temperature of 0 to 30° C., preferably to a temperature of 0 to 10° C., in the step (2). If the mixture is cooled to the above temperature range, it is advantageous in that the reduction of the yield of the crystalline form (I) of the mesylate salt represented by the above Formula 1 can be minimized.

In another aspect of the present invention, the residual mixture may be dried at a temperature of 30 to 70° C. after the cooling in the step (2). If the residual mixture is dried at the above temperature range, it is advantageous in that the solvent residue can be effectively removed.

In addition, the present invention provides a pharmaceutical composition for treating a protein kinase-mediated disorder, which comprises the mesylate salt represented by the above Formula 1 and a pharmaceutically acceptable additive.

Further, the present invention provides a pharmaceutical composition for inhibiting epidermal growth factor receptor (EGFR) having one or more mutations as compared with wild-type EGFR, which comprises the mesylate salt represented by the above Formula 1 and a pharmaceutically acceptable additive.

In one aspect of the invention, the mutation may be Del E746-A750, L858R, or T790M, and it may be dual mutations selected from Del E746-A750/T790M or L858R/T790M.

In one aspect of the present invention, the pharmaceutical composition may be used for the prevention or treatment of allograft rejection, a graft versus host disorder, diabetic retinopathy, choroidal neovascularization due to age-related age-related macular degeneration, psoriasis, arthritis, osteoarthritis, rheumatoid arthritis, synovial pannus formation in arthritis, multiple sclerosis, myasthenia gravis, diabetes mellitus, a diabetic vascular disorder, retinopathy of prematurity, infant hemangioma, non-small cell lung cancer, bladder cancer, head and neck cancer, prostate cancer, breast cancer, ovarian cancer, stomach cancer, pancreatic cancer, fibrosis, atherosclerosis, restenosis, an autoimmune disorder, allergy, a respiratory disorder, asthma, transplant rejection, inflammation, thrombosis, retinal vessel proliferation, an inflammatory bowel disorder, Crohn's disease, ulcerative colitis, a bone disorder, graft or bone marrow transplant rejection, lupus, chronic pancreatitis, cachexia, septic shock, a fibroproliferative and differentiating skin disease or disorder, a central nervous system disorder, a neurodegenerative disorder, Alzheimer's disease, Parkinson's disease, a disorder or condition associated with nerve damage following brain or spinal cord injury or exon degeneration, acute or chronic cancer, an ocular disorder, viral infection, a heart disorder, a pulmonary disorder or a kidney disorder, and bronchitis. Preferably, the pharmaceutical composition may be used for the prevention or treatment of acute or chronic cancer, more preferably lung cancer, most preferably non-small cell lung cancer or brain metastatic non-small cell lung cancer, but is not limited thereto.

In one aspect of the invention, the pharmaceutical composition can inhibit the epidermal growth factor receptor (EGFR) having at least one mutation as compared to a wild-type EGFR, and thus can be used for the prevention or treatment of the disease.

A compound of the present invention may be administered alone or as a part of a pharmaceutical composition in a therapeutically effective amount, and the pharmaceutical composition facilitates administration of the compound into an organism. In addition, the compound and the composition may be administered alone or in combination with one or more additional therapeutic agents. There are a variety of techniques for administering the compound and composition, which include intravenous administration, inhalation, oral administration, rectal administration, parenteral, intravitreal administration, subcutaneous administration, intramuscular administration, intranasal administration, transdermal administration, topical administration, ocular administration, buccal administration, tracheal administration, bronchial administration, sublingual administration or optic nerve administration, but are not limited thereto. The compound provided herein is administered as a pharmaceutical dosage form publicly known, for example, a tablet, a capsule or an elixir for oral administration, a suppository for rectal administration, a sterile solution or a suspension for parenteral or intramuscular administration, a lotion, a gel, an ointment or a cream for topical administration, etc.

A preferred dosage of the mesylate salt represented by the Formula (1) contained in the pharmaceutical composition of the present invention varies depending on the condition and the weight of a patient, the degree of a disease, the type of a drug, the route and duration of administration, but the dosage may be appropriately selected by a person of ordinary skill in the art. Generally, the preferred dosage of the mesylate salt represented by Formula (I) may range from about 10 mg/day to about 1000 mg/day.

As the pharmaceutically acceptable additive to be employed in the pharmaceutical composition of the present invention, at least one diluent or excipient commonly used such as a wetting agent, a disintegrant, a lubricant, a binder, a surfactant, and the like may be used.

The pharmaceutically acceptable additive may include Kollidon, shellac, gum arabic, talc, titanium oxide, sugar (e.g., sugar cane), gelatin, water, a polysaccharide such as lactose or glucose, paraffin (e.g., a petroleum fraction), a vegetable oil (e.g., peanut oil or sesame oil), and a pharmaceutically acceptable organic solvent such as an alcohol (e.g., ethanol or glycerol), a natural mineral powder (e.g., kaolin, clay, talc, and chalk), a synthetic mineral powder (e.g., highly dispersed silicic acid and silicate), an emulsifier (e.g., lignin, sulfite liqueur, methylcellulose, starch, and polyvinylpyrrolidone), magnesium stearate, stearic acid, sodium lauryl sulfate, and the like, but is not limited thereto.

The present invention provides a use of the mesylate salt represented by the above Formula 1 for the manufacture of a medicament for treating a protein kinase-mediated disorder.

Also, the present invention provides a use of the mesylate salt represented by the above Formula 1 for the manufacture of a medicament for inhibiting the activity of epidermal growth factor receptor (EGFR) having at least one mutation as compared with wild-type EGFR.

The present invention provides a method for treating a protein kinase-mediated disorder, which comprises the step of administering the mesylate salt represented by the above Formula 1 to a subject.

Also, the present invention provides a method for inhibiting the activity of epidermal growth factor receptor (EGFR) having at least one mutation as compared with wild-type EGFR, which comprises the step of administering the mesylate salt represented by the above Formula 1 to a subject.

MODE FOR THE INVENTION

Hereinafter, preferred examples of the present invention will be provided in order to facilitate understanding of the present invention. However, these examples merely illustrate the present invention, and it will be apparent to one skilled in the art that various changes and modifications may be made within the scope of the present invention and the technical idea thereof and that such variations and modifications are within the scope of the appended claims.

Example

Example 1: Preparation of Mesylate Salt of N-(5-(4-(4-((dimethylamino)methyl)-3-phenyl-1H-pyrazol-1-yl)pyrimidine-2-ylamino)-4-methoxy-2-morpholinophenyl)acrylamide A reactor was charged with N-(5-(4-(4-((dimethylamino)methyl)-3-phenyl-1H-pyrazol-1-yl)pyrimidine-2-ylamino)-

4-methoxy-2-morpholinophenyl)acrylamide (1,100.0 g, 1,983.2 mmol) prepared by the same process as disclosed in WO 2016-060443, acetone (4.4 L), and purified water (1.1 L), which were stirred while heated to 45 to 55° C. Methanesulfonic acid (186.8 g, 1,943.6 mmol) was diluted in purified water (0.55 L), which was added dropwise thereto while kept at 45° C. or higher. Then, the mixture was stirred for 30 minutes or longer to prepare the mixture of mesylate salt of N-(5-(4-(4-((dimethylamino)methyl)-3-phenyl-1H-pyrazol-1-yl)pyrimidine-2-ylamino)-4-methoxy-2-morpholinophenyl)acrylamide.

Then, in order to crystallize the mesylate salt in the mixture, acetone (8.8 L) was added dropwise at 40 to 50° C., stirred for 30 minutes or more, cooled to 0 to 5° C. and stirred for 3 hours or more. Acetone (8.8 L) was added dropwise thereto while kept at 40 to 50° C., and the mixture was stirred for 30 minutes or more, cooled to 0 to 5° C., and stirred for 3 hours or more. The reaction mixture was filtered under a reduced pressure, and the wet cake was then washed with acetone (5.5 L). The solid thus obtained was vacuum dried at 55° C. to obtain 1,095.8 g of the title compound (yield: 84.9%).

The results of measurement of the title compound with 1H-NMR (400 MHZ, DMSO-$d_6$) are as follows:

1H-NMR (400 MHZ, DMSO-$d_6$) δ 9.79 (s, 1H), 9.35 (s, 1H), 9.21 (s, 1H), 8.78 (s, 1H), 8.59 (d, 1H), 8.33 (s, 1H), 7.77 (d, 2H), 7.55 (m, 3H), 7.34 (d, 1H), 6.94 (s, 1H), 6.71-6.76 (q, 1H), 6.28-6.31 (d, 1H), 5.81-5.83 (d, 1H), 4.48 (s, 2H), 3.90 (s, 3H), 3.81-3.83 (t, 4H), 2.86-2.88 (t, 4H), 2.66 (s, 6H), 2.35 (s, 3H).

The title compound was measured by differential scanning calorimetry (DSC). As a result, the DSC graph had an endothermic transition peak at about 217° C. The DSC measurement was performed using a Mettler Toledo DSC 1 STAR (sample vessel: a sealed aluminum pan under the conditions of 99% nitrogen and a temperature elevation from 30° C. to 300° C. at a rate of 10° C./min).

The title compound was measured by PXRD, which revealed that the diffraction peaks in the PXRD graph were present at 2θ angles of 5.614, 12.394, 14.086, 17.143, 18.020, 19.104, 21.585, 22.131, and 22.487 degrees (see FIG. 1). The PXRD spectrum of the compound was obtained using a Bruker D8 advance (X-ray source: CuKα, tube voltage: 40 kV/tube current: 40 mA, divergent slit: 0.3, and scattering slit: 0.3).

Comparative Example 1: Preparation of N-(5-(4-(4-((dimethylamino)methyl)-3-phenyl-1H-pyrazol-1-yl)pyrimidine-2-ylamino)-4-methoxy-2-morpholinophenyl)acrylamide in the Form of a Free Base N-(5-(4-(4-((dimethylamino)methyl)-3-phenyl-1H-pyrazol-1-yl)pyrimidine-2-ylamino)-4-methoxy-2-morpholinophenyl)acrylamide in the form of a free base was prepared by the same process as disclosed in WO 2016-060443.

Comparative Example 2: Preparation of Hydrochloride Salt of N-(5-(4-(4-((dimethylamino)methyl)-3-phenyl-1H-pyrazol-1-yl)pyrimidine-2-ylamino)-4-methoxy-2-morpholinophenyl)acrylamide A reactor was charged with N-(5-(4-(4-((dimethylamino)methyl)-3-phenyl-1H-pyrazol-1-yl)pyrimidine-2-ylamino)-4-methoxy-2-morpholinophenyl)acrylamide (50.00 g, 90.1 mmol) prepared by the same process as disclosed in WO 2016-060443, acetone (450 mL), and purified water (50 mL), which were cooled to 0 to 5° C. Hydrochloric acid (9.39 g, 90.1 mmol) was diluted in acetone (50 mL), which was added dropwise thereto while kept at 0 to 5° C. Then, the mixture was adjusted to 20 to 25° C. and stirred for 2 hours or more. The reaction mixture was filtered under a reduced pressure, and the solid thus obtained was vacuum dried to obtain 49.91 g of the title compound (yield: 93.7%).

The title compound was measured under the same conditions as in Example 1. The results of measurement with 1H-NMR (400 MHZ, DMSO-$d_6$) are as follows:

1H-NMR (400 MHZ, DMSO-$d_6$) δ 10.82 (s, 1H), 9.36 (s, 1H), 9.26 (s, 1H), 8.69 (s, 1H), 8.57 (d, 1H), 8.39 (s, 1H), 7.77 (d, 2H), 7.49-7.57 (m, 3H), 7.33 (d, 1H), 6.94 (s, 1H), 6.69-6.76 (q, 1H), 6.28 (d, 1H), 5.78 (d, 1H), 4.42 (d, 2H), 3.89 (s, 3H), 3.81 (s, 4H), 2.88 (s, 4H), 2.58 (d, 6H)

Comparative Example 3: Preparation of Citrate Salt of N-(5-(4-(4-((dimethylamino)methyl)-3-phenyl-1H-pyrazol-1-yl)pyrimidine-2-ylamino)-4-methoxy-2-morpholinophenyl)acrylamide A reactor was charged with N-(5-(4-(4-((dimethylamino)methyl)-3-phenyl-1H-pyrazol-1-yl)pyrimidine-2-ylamino)-4-methoxy-2-morpholinophenyl)acrylamide (15.00 g, 27.0 mmol) prepared by the same process as disclosed in WO 2016-060443 and ethyl acetate (600 mL), which were stirred with reflux to dissolve the reaction mixture. Citric acid (5.68 g, 29.6 mmol) was dissolved in acetone (25 mL), which was added dropwise thereto at 50 to 70° C. Then, the reaction mixture was cooled to 20 to 30° C. and stirred for 2 hours or more. The reaction mixture was filtered under a reduced pressure, and the wet cake was then washed with ethyl acetate (300 mL). The solid thus obtained was vacuum dried to obtain 20.15 g of N-(5-(4-(4-((dimethylamino)methyl)-3-phenyl-1H-pyrazol-1-yl)pyrimidine-2-ylamino)-4-methoxy-2-morpholinophenyl)acrylamide 2-hydroxypropane-1,2,3-tricarboxylate salt as a crude compound (yield: 99.8%).

A reactor was charged with the crude compound of N-(5-(4-(4-((dimethylamino)methyl)-3-phenyl-1H-pyrazol-1-yl)pyrimidine-2-ylamino)-4-methoxy-2-morpholinophenyl)acrylamide 2-hydroxypropane-1,2,3-tricarboxylate salt (18.70 g) and purified water (187 mL), which were stirred at 20 to 30° C. for 2 hours or more. The reaction mixture was filtered under a reduced pressure, and the solid thus obtained was vacuum dried to obtain 15.67 g of the title compound (yield: 83.8%).

The title compound was measured under the same conditions as in Example 1. The results of measurement with 1H-NMR (400 MHZ, DMSO-$d_6$) are as follows:

1H-NMR (400 MHZ, DMSO-$d_6$) δ 9.22 (s, 1H), 9.17 (s, 1H), 8.97 (s, 1H), 8.54 (d, 1H), 8.24 (s, 1H), 7.93 (d, 2H), 7.43-7.53 (m, 3H), 7.33 (d, 1H), 6.95 (s, 1H), 6.71-6.78 (q, 1H), 6.36 (d, 1H), 5.82 (d, 1H), 3.90 (s, 3H), 3.82 (s, 6H), 2.86 (s, 4H), 2.50-2.71 (d, 4H), 2.37 (s, 6H)

Comparative Example 4: Preparation of Esilate Salt of N-(5-(4-(4-((dimethylamino)methyl)-3-phenyl-1H-pyrazol-1-yl)pyrimidine-2-ylamino)-4-methoxy-2-morpholinophenyl)acrylamide A reactor was charged with N-(5-(4-(4-((dimethylamino)methyl)-3-phenyl-1H-pyrazol-1-yl)pyrimidine-2-ylamino)-4-methoxy-2-morpholinophenyl)acrylamide (15.00 g, 27.0 mmol) prepared by the same process as disclosed in WO 2016-060443 and tetrahydrofuran (300 mL), which were stirred. Ethanesulfonic acid (2.98 g, 27.1 mmol) was diluted in tetrahydrofuran (45 mL), which was added dropwise thereto while kept at 20 to 25° C. Then, the reaction mixture was stirred at room temperature for 11 hours or more. The reaction mixture was filtered under a reduced pressure, and the solid thus obtained was vacuum dried to obtain 16.20 g of esilate salt of N-(5-(4-(4-((dimethylamino)methyl)-3-phenyl-1H-pyrazol-1-yl)pyrimidine-2-ylamino)-4-methoxy-2-morpholinophenyl)acrylamide (yield: 90.1%) as the title compound.

The title compound of N-(5-(4-(4-((dimethylamino)methyl)-3-phenyl-1H-pyrazol-1-yl)pyrimidine-2-ylamino)-4-methoxy-2-morpholinophenyl)acrylamide esilate was measured under the same conditions as in Example 1. The results of measurement with 1H-NMR (400 MHZ, DMSO-$d_6$) are as follows:

1H-NMR (400 MHZ, DMSO-$d_6$) δ 9.69 (s, 1H), 9.34 (s, 1H), 9.22 (s, 1H), 8.75 (s, 1H), 8.58 (d, 1H), 8.36 (s, 1H), 7.77 (d, 2H), 7.52-7.58 (q, 3H), 7.33 (d, 1H), 6.94 (s, 1H), 6.69-6.76 (q, 1H), 6.26 (d, 1H), 5.80 (d, 1H), 4.46 (s, 2H), 3.89 (s, 3H), 3.82 (s, 4H), 2.87 (s, 4H), 2.65 (s, 6H), 2.34-2.39 (q, 2H), 1.03-1.06 (t, 3H)

Test Example

Test Example 1: Solubility Test

The compounds prepared in Example 1 and Comparative Example 1 were tested for solubility depending on pH, and the solubilities in artificial gastric fluid, artificial intestinal fluid, water, and ethanol were compared.

120 mg of the compound (corresponding to 100 mg as the compound of the Formula 2) prepared in Example 1 was added to 5 mL of a buffer solution having each of pHs described in Table 1 below, artificial gastric fluid, artificial intestinal fluid, water, or ethanol, which was stirred in a 37° C. water bath under a condition of 50 rpm for 12 hours. In addition, 100 mg of the compound prepared in Comparative Example 1 was tested in the same condition as in the above. After the stirring, a concentration of the dissolved compound represented by the Formula 2 was measured, and solubilities of the compounds prepared in Example 1 and Comparative Example 1 were relatively compared. The results are shown in FIG. 3 and Table 1 below.

Figure 3:
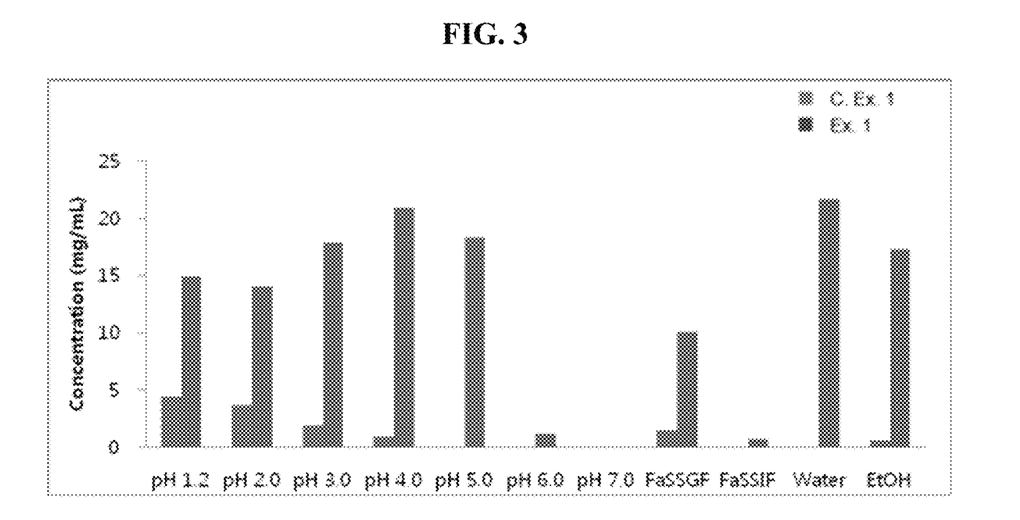
FIG. 3 is a graph showing the results of solubility tests of the compound prepared in Comparative Example 1 (left) and those of the compound prepared in Example 1 (right) (FaSSGF: artificial gastric fluid, FaSSIF: artificial intestinal fluid).
Figure 4:
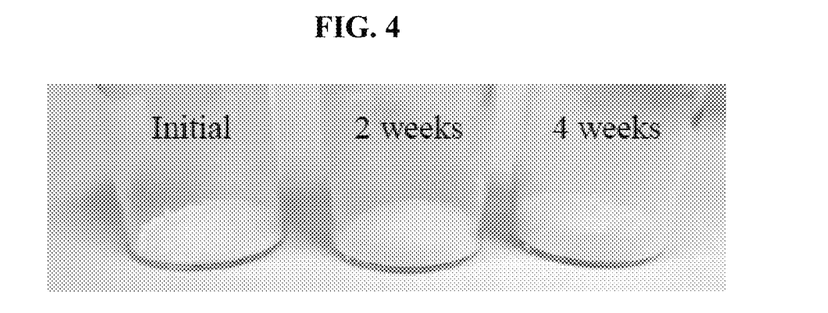
FIG. 4 is a photograph showing the results of stability tests carried out under stress conditions for the compound prepared in Example 1 (Initial: at start, 2 weeks: after 2 weeks, 4 weeks: after 4 weeks).
Figure 5:
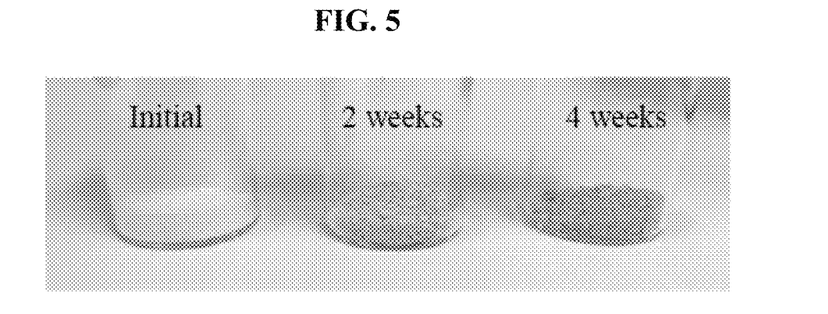
FIG. 5 is a photograph showing the results of stability tests carried out under stress conditions for the compound prepared in Comparative Example 2 (Initial: at start, 2 weeks: after 2 weeks, 4 weeks: after 4 weeks).
Figure 6:
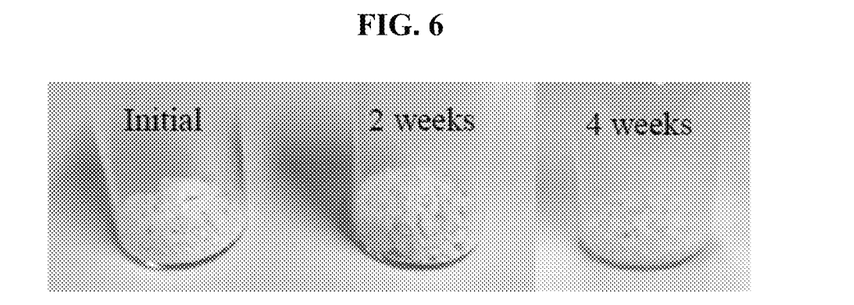
FIG. 6 is a photograph showing the results of stability tests carried out under stress conditions for the compound prepared in Comparative Example 3 (Initial: at start, 2 weeks: after 2 weeks, 4 weeks: after 4 weeks).
Figure 7:
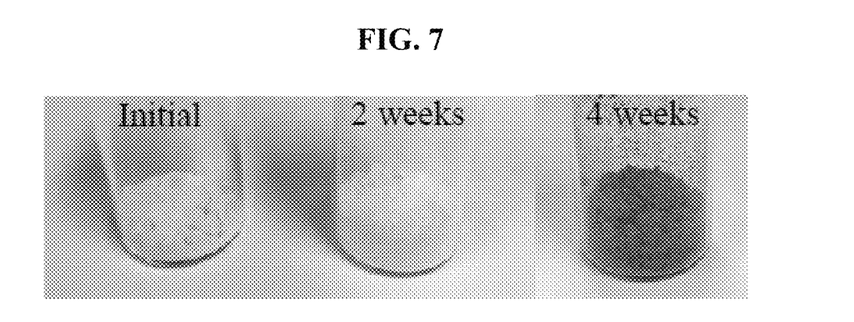
FIG. 7 is a photograph showing the results of stability tests carried out under stress conditions for the compound prepared in Comparative Example 4 (Initial: at start, 2 weeks: after 2 weeks, 4 weeks: after 4 weeks).
Figure 8:
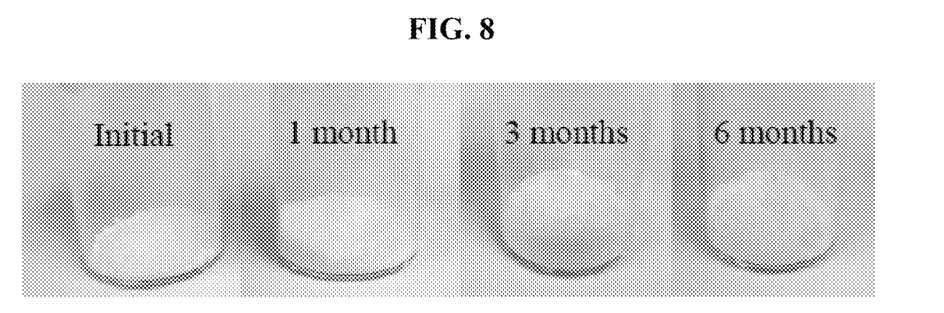
FIG. 8 is a photograph showing the results of stability tests carried out under accelerated conditions for the compound prepared in Example 1 (Initial: at start, 1 month: after 1 month, 3 months: after 3 months, 6 months: after 6 months).
Figure 9:
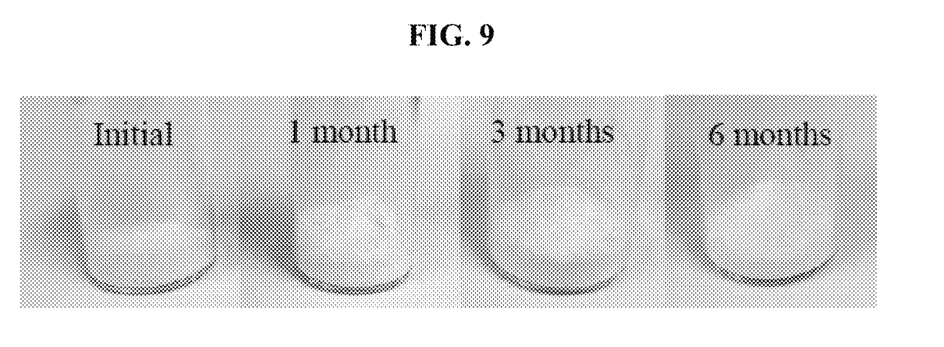
FIG. 9 is a photograph showing the results of stability tests carried out under accelerated conditions for the compound prepared in Comparative Example 2 (Initial: at start, 1 month: after 1 month, 3 months: after 3 months, 6 months: after 6 months).
Figure 10:
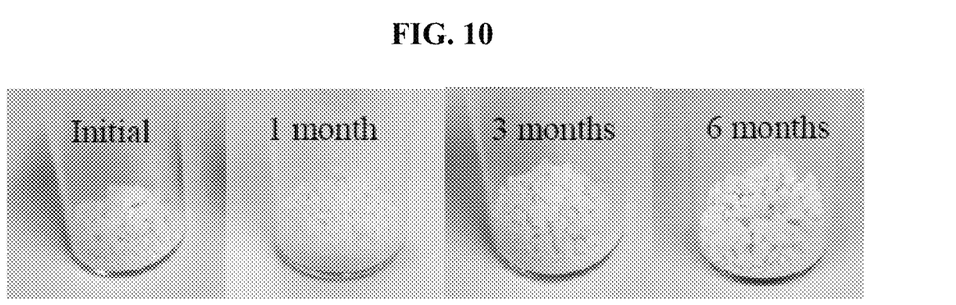
FIG. 10 is a photograph showing the results of stability tests carried out under accelerated conditions for the compound prepared in Comparative Example 3 (Initial: at start, 1 month: after 1 month, 3 months: after 3 months, 6 months: after 6 months).
Figure 11:
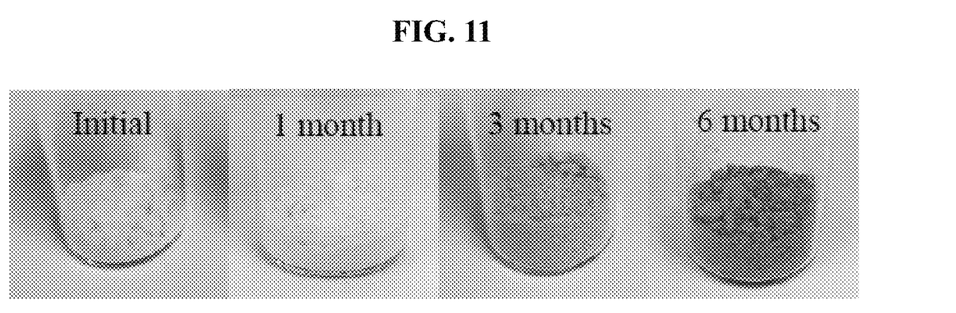
FIG. 11 is a photograph showing the results of stability tests carried out under accelerated conditions for the compound prepared in Comparative Example 4 (Initial: at start, 1 month: after 1 month, 3 months: after 3 months, 6 months: after 6 months).

As shown in FIG. 3 and Table 1 above, the compound in the mesylate salt form prepared in Example 1 had a solubility of at least 20,000 times higher in water, a solubility of about 10 times higher in artificial gastric fluid (FaSSGF), and a solubility of about 25 times higher in artificial intestinal fluid (FaSSIF) than that of the compound in the free base form prepared in Comparative Example 1.

Test Examples 2 and 3: Stability Test

The compounds prepared in Example 1 and Comparative Examples 2 to 4 were each tested for stability. The five compounds were tested for stability under stress conditions and accelerated conditions. The two conditions are specifically shown in Table 2 below.

TABLE 2

| | Stress conditions | Accelerated conditions |
|---|---|---|
| Temperature | 60 ± 2° C. | 40 ± 2° C. |
| Humidity | 75 ± 5% (relative humidity) | 75 ± 5% (relative humidity) |
| Container | A glass vial of 10 mL and a rubber cap | A polyethylene double bag and a high-density polyethylene (HDPE) bottle |
| Sampling timing | At start and after two and four weeks | At start and after 1, 3, and 6 months |

Test Example 2: Stability Test of the Compounds Prepared in Example 1 and Comparative Examples 2 to 4 Under Stress Conditions The compounds prepared in Example 1 and Comparative Examples 2 to 4 were each tested for stability under the stressed conditions as given in Table 2 above. The results are shown in FIGS. 4 to 7 and Tables 3 and 4 below. The conditions for the PXRD and DSC measurements are the same as described in Example 1.

TABLE 1

| | Solubility (mg/mL) | | | | | | | | | | |
|---|---|---|---|---|---|---|---|---|---|---|---|
| | pH 1.2 | pH 2.0 | pH 3.0 | pH 4.0 | pH 5.0 | pH 6.0 | pH 7.0 | Artificial gastric fluid (FaSSGF) | Artificial intestinal fluid (FaSSIF) | Water | Ethanol |
| C. Ex. 1 | 4.4 | 3.7 | 1.9 | 1.0 | 0.01 | 0.003 | 0.001 | 1.5 | 0.027 | 0.001 | 0.599 |
| Ex. 1 | 14.9 | 14.1 | 17.9 | 20.9 | 18.4 | 1.2 | 0.018 | 10.1 | 0.68 | 21.6 | 17.3 |

TABLE 3

| | PXRD pattern | | | DSC onset (° C.) | | | Appearance (color) | | |
|---|---|---|---|---|---|---|---|---|---|
| | Start | 2 weeks | 4 weeks | Start | 2 weeks | 4 weeks | Start | 2 weeks | 4 weeks |
| Ex. 1 | — | Same pattern | Same pattern | 214 | 214 | 214 | White | White | White |
| C. Ex. 2 | — | Pattern changed | Pattern changed | 267 | 269 | 269 | Yellow | Light brown | Light grey to violet |
| C. Ex. 3 | — | Pattern changed | Pattern changed | 182 | 182 | 181 | Light yellow | Light yellow | Light yellow |
| C. Ex. 4 | — | Same pattern | Pattern changed | 223 | 222, 227 | 172, 193, 219 | Yellow | Light yellow | Violet |

In addition, the results of high-performance liquid chromatography (HPLC) measurement are shown in Table 4 below, and the measurement conditions are as follows:

Moving phase buffer: 250 mM of ammonium acetate in water (moving phase A: buffer/water/acetonitrile, moving phase B: acetonitrile, column: Xbridge BEH C18 XP).

TABLE 4

| | Purity (%) | | | | Content (%) | | | | Water content (%) | | | |
|---|---|---|---|---|---|---|---|---|---|---|---|---|
| | Start | 2 weeks | 4 weeks | Change | Start | 2 weeks | 4 weeks | Change | Start | 2 weeks | 4 weeks | Change |
| Ex. 1 | 99.2 | 99.3 | 99.3 | +0.1 | 98.8 | 97.7 | 98.9 | +0.1 | 2.48 | 2.71 | 2.70 | +0.22 |
| C. Ex. 2 | 99.0 | 99.1 | 99.1 | +0.1 | 97.4 | 96.2 | 95.2 | −2.2 | 0.86 | 1.23 | 1.44 | +0.58 |
| C. Ex. 3 | 99.2 | 98.8 | 98.7 | −0.5 | 100.0 | 98.9 | 98.6 | −1.4 | 0.65 | 0.62 | 1.47 | +0.82 |
| C. Ex. 4 | 99.5 | 99.0 | 98.9 | −0.6 | 96.5 | 94.7 | 89.5 | −7 | 1.15 | 1.37 | 3.81 | +2.03 |

Test Example 3: Stability Test of the Compounds Prepared in Example 1 and Comparative Examples 2 to 4 Under Accelerated Conditions The compounds prepared in Example 1 and Comparative Examples 2 to 4 were each tested for stability under the accelerated conditions as given in Table 2 above. The results are shown in FIGS. 8 to 11 and Tables 5 and 6 below. The conditions for the PXRD and DSC measurements are the same as described in Example 1.

TABLE 5

| | PXRD pattern | | | | DSC onset (° C.) | | | | Appearance (color) | | | |
|---|---|---|---|---|---|---|---|---|---|---|---|---|
| | Start | 1 month | 3 months | 6 months | Start | 1 mo | 3 mos | 6 mos | Start | 1 mo | 3 mos | 6 mos |
| Ex. 1 | — | Same pattern | Same pattern | Same pattern | 214 | 214 | 214 | 214 | W | W | W | W |
| C. Ex. 2 | — | Pattern changed | Pattern changed | Pattern changed | 267 | 272 | 271 | 271 | Y | Y | Y | LY |
| C. Ex. 3 | — | Same pattern | Pattern changed | Pattern changed | 182 | 182 | 180 | 183 | LY | LY | LY | LY |
| C. Ex. 4 | — | Same pattern | Same pattern | Same pattern | 223 | 222 | 219 | 218 | Y | LY | LV | V |

W: white,
Y: yellow,
LY: light yellow,
V: violet,
LV: light violet

In addition, the results of high-performance liquid chromatography (HPLC) measurement are shown in Table 6 below, and the measurement conditions are as described in Test Example 2:

TABLE 6

| | Purity (%) | | | | | Content (%) | | | | | Water content (%) | | | | |
|---|---|---|---|---|---|---|---|---|---|---|---|---|---|---|---|
| | Start | 1 mo | 3 mos | 6 mos | Change | Start | 1 mo | 3 mos | 6 mos | Change | Start | 1 mo | 3 mos | 6 mos | Change |
| Ex. 1 | 99.2 | 99.3 | 99.3 | 99.3 | +0.1 | 98.8 | 98.9 | 98.9 | 99.1 | +0.3 | 2.48 | 2.73 | 3.19 | 3.01 | +0.53 |
| C. Ex. 2 | 99.0 | 99.0 | 98.9 | 98.8 | −0.2 | 97.4 | 97.0 | 98.3 | 97.6 | +0.2 | 0.86 | 0.98 | 1.47 | 1.28 | +0.42 |
| C. Ex. 3 | 99.2 | 98.9 | 98.9 | 97.7 | −1.5 | 100.0 | 100.5 | 101.0 | 98.7 | −1.3 | 0.65 | 0.83 | 3.05 | 3.50 | +2.85 |
| C. Ex. 4 | 99.5 | 99.1 | 99.0 | 98.4 | −1.1 | 96.5 | 96.1 | 95.1 | 91.4 | −5.1 | 1.15 | 2.48 | 2.98 | 3.17 | +2.02 |

From the results of the above stability test, the compound prepared in Example 1 was excellent in stability since it showed few changes in purity and water content at the start and at the end of the stability test, no change in PXRD patterns, and no change in appearance observed in color. In contrast, the compounds of Comparative Examples 2 to 4 were poor in stability since they showed greater changes in purity and water content than the compound prepared in Example 1, and some changes in PXRD patterns and in appearance were observed.

Test Example 4: Pharmacokinetic Comparison Test for the Compounds Prepared in Example 1 and Comparative Example 1 in Normal Rats and Rats Treated with Esomeprazole The compounds prepared in Example 1 and Comparative Example 1 were each tested for pharmacokinetic in normal rats and rats treated with esomeprazole, which is a proton pump inhibitor. Specifically, the maximum plasma concentration ($C_{max}$) and the area under the plasma concentration curve ($AUC_{last}$) in the normal rats and the rats treated with esomeprazole were compared to evaluate the absorption of the drugs in the actual animals.

In order to compare the pharmacokinetic parameters, 8-week old male rats (SD rats) with a body weight of about 250 g were used as test animals. And the compounds prepared in Example 1 and Comparative Example 1 were each suspended in 0.5% methylcellulose and orally administered to normal rats at a dose of 30 mg/5 ml/kg.

Figure 12:
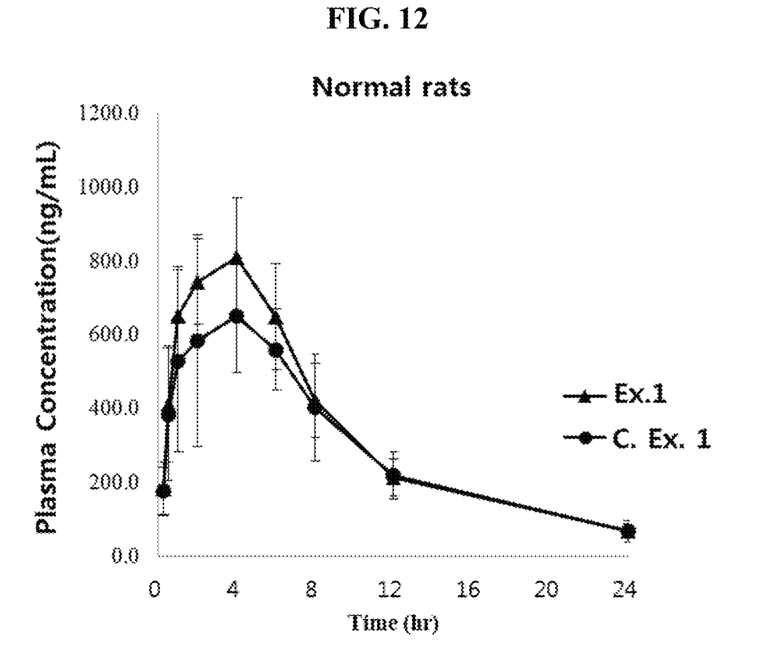
FIG. 12 is a graph showing the results of pharmacokinetic comparison tests carried out on normal rats in Test Example 4.
Figure 13:
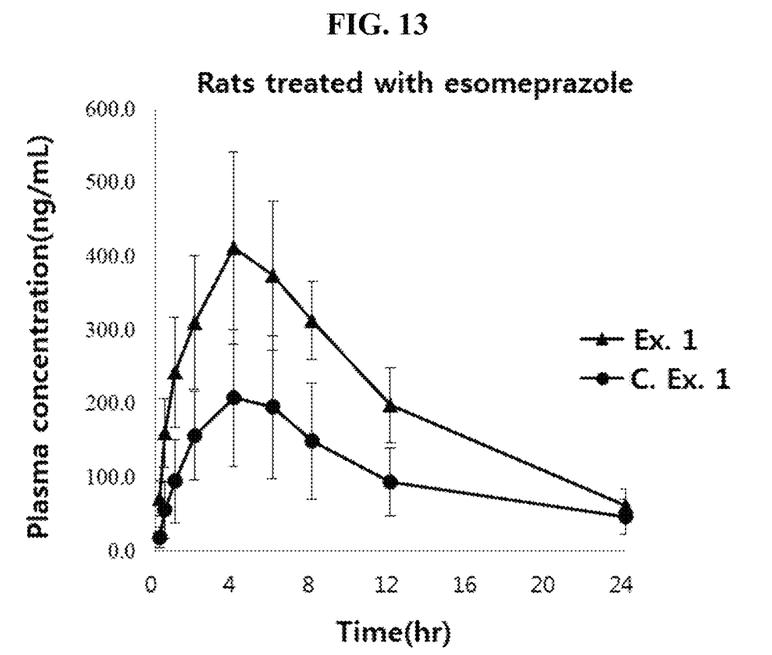
FIG. 13 is a graph showing the results of pharmacokinetic comparison tests carried out on rats treated with esomeprazole in Test Example 4.

Meanwhile, esomeprazole(esomeprazole magnesium dihydrate, Sigma-Aldrich) was intravenously administered to 8-week old male rats with a body weight of about 250 g at a dose of 5 mg/2 mL/kg for 3 days, and the compounds prepared in Example 1 and Comparative Example 1 were each orally administered to the rats at the same dose as that administered to the normal rats (i.e., 30 mg/5 ml/kg). A comparison of the pharmacokinetic parameters (i.e., the maximum plasma concentration and the area under the plasma concentration curve) calculated therefrom are shown in Table 7 and FIGS. 12 and 13.

TABLE 7

| Pharmacokinetic parameter | Normal rats | | Rats treated with esomeprazole | |
|---|---|---|---|---|
| | Ex. 1 | C. Ex. 1 | Ex. 1 | C. Ex. 1 |
| Maximum plasma concentration ($C_{max}$, ng/mL) | 815.6 | 725.7 | 427.5 | 223.0 |
| Area under the plasma concentration curve ($AUC_{last}$, ng · hr/mL) | 8139.0 | 7293.6 | 5210.9 | 2636.7 |

As shown in the above results, a maximum plasma concentration and an area under the plasma concentration curve of the compound in the free base form (Comparative Example 1) in normal rats were lower than those of the compound in the mesylate salt form (Example 1) by 11.0% and 10.4%, respectively. A maximum plasma concentration and an area under the plasma concentration curve of the former in the rats treated with esomeprazole were lower than those of the latter by 47.8% and 49.4%, respectively. That is, it was confirmed that the compound prepared in Comparative Example 1 has a lower exposure to the rats than that of the compound prepared in Example 1.

In addition, the maximum plasma concentration and the area under the plasma concentration curve of the compound prepared in Example 1 were reduced in the esomeprazole-treated rats by 47.6% and 36.0%, respectively, as compared with the normal rats. In contrast, the maximum plasma concentration and the area under the plasma concentration curve of the compound prepared in Comparative Example 1 were reduced in the esomeprazole-treated rats by 69.3% and 63.8%, respectively, as compared with the normal rats. It was confirmed from these results that the compound prepared in Example 1 has fewer changes in pharmacokinetic due to the esomeprazole administration than those of the compound prepared in Comparative Example 1; therefore, the former maintains a high plasma concentration in rats.

Figure 14:
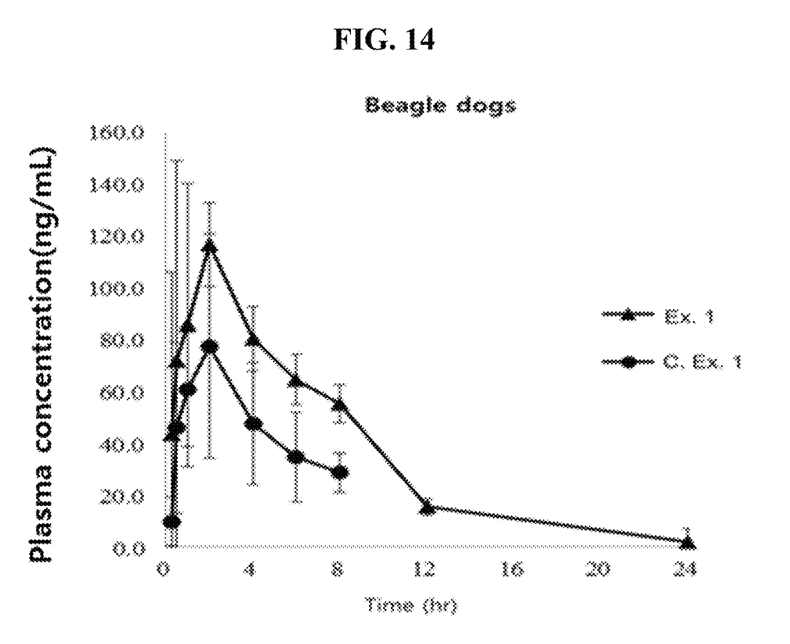
FIG. 14 is a graph showing the results of pharmacokinetic comparison tests carried out on beagle dogs in Test Example 5.

Test Example 5: Pharmacokinetic Comparison Test for the Compounds Prepared in Example 1 and Comparative Example 1 in Beagle Dogs In order to compare the pharmacokinetic parameters, 15 to 17-month old male beagle dog with a body weight of about 10 kg were used as test animals, and the compounds prepared in Example 1 and Comparative Example 1 were each suspended in 0.5% methylcellulose and orally administered to beagle dogs at a dose of 5 mg/2 mL/kg. A comparison of the pharmacokinetic parameters (i.e., the maximum plasma concentration and the area under the plasma concentration curve) calculated therefrom are shown in Table 8 and FIG. 14.

TABLE 8

|  | Ex. 1 | C. Ex. 1 |
| --- | --- | --- |
| Maximum plasma concentration ($C_{max}$, ng/mL) | 134.7 | 80.7 |
| Area under the plasma concentration curve ($AUC_{last}$, ng · hr/mL) | 811.5 | 379.1 |

As shown in the above results, a maximum plasma concentration and an area under the plasma concentration curve of the compound in the free base form (Comparative Example 1) in beagle dogs were lower than those of the compound in the mesylate salt form (Example 1) by 40.1% and 50.4%, respectively. It was confirmed from these results that the compound prepared in Example 1 showed a higher exposure than the compound prepared in Comparative Example 1 in beagle dogs.

As described above, the mesylate salt compound of N-(5-(4-(4-((dimethylamino)methyl)-3-phenyl-1H-pyrazol-1-yl)pyrimidine-2-ylamino)-4-methoxy-2-morpholinophenyl)acrylamide according to the present invention produces excellent effects in that it is excellent in solubility and bioavailability as compared with the free base compound of N-(5-(4-(4-((dimethylamino)methyl)-3-phenyl-1H-pyrazol-1-yl)pyrimidine-2-ylamino)-4-methoxy-2-morpholinophenyl)acrylamide, that it is improved in stability, solubility, and bioavailability as compared with other pharmaceutically acceptable salts thereof, and that it has a high purity.

Hereinbefore, the present invention has been explained based on the preferred example. However, it will be apparent to one skilled in the art that various changes and modifications may be made without departing from the technical idea of the present invention as described in the claims by adding, modifying, and deleting the constitutional elements and that such variations and modifications are within the scope of the present invention.

What is claimed:

1. A process for preparing a mesylate salt of Formula 1

[Formula 1]

which comprises:

(1) mixing the compound represented by the following Formula 2

[Formula 2]

and a single organic solvent or a mixed solvent, followed by adding methanesulfonic acid thereto, to prepare a mixture of the mesylate salt represented by the Formula 1; and (2) adding an organic solvent to the mixture to crystallize the mesylate salt according to Formula 1.

2. The process of claim 1, wherein the single organic solvent used in the step (1) is one selected from the group consisting of acetone, methyl ethyl ketone, and ethyl acetate.

3. The process of claim 1, wherein the mixed solvent used in the step (1) is a mixed solvent of water and at least one organic solvent selected from acetone and methyl ethyl ketone.

4. The process of claim 3, wherein the mixed ratio of water and the organic solvent is 1:1 to 1:10 by volume.

5. The process of claim 1, wherein the step (1) is carried out at a temperature of 20 to 70° C.

6. The process of claim 1, wherein the step (1) is carried out at a temperature of 45 to 60° C.

7. The process of claim 1, wherein the organic solvent used in the step (2) is at least one selected from the group consisting of acetone, methyl ethyl ketone, and ethyl acetate.

8. The process of claim 1, wherein in the step (2), the organic solvent is added in a volume ranging from 3 mL to 20 mL based on 1 g of the compound represented by the Formula 2.

* * * * *